United States Patent [19]

Cranston

[11] 4,403,176

[45] Sep. 6, 1983

[54] CIRCUIT FOR DRIVING AN ULTRASONIC DENTAL TOOL AT ITS RESONANT FREQUENCY

[75] Inventor: Dale O. Cranston, Lawrence, Kans.

[73] Assignee: California Technics, Ltd., Olathe, Kans.

[21] Appl. No.: 66,470

[22] Filed: Aug. 13, 1979

Related U.S. Application Data

[63] Continuation of Ser. No. 903,888, May 8, 1978, abandoned.

[51] Int. Cl.³ .............................................. H02K 33/00
[52] U.S. Cl. .................................... 318/114; 318/129; 318/130; 318/132
[58] Field of Search ................ 318/130, 132, 122–129, 318/114, 115, 37, 116, 118; 361/203; 433/119

[56] References Cited

U.S. PATENT DOCUMENTS

| 2,995,689 | 8/1961 | Scarpa | 318/37 |
| 3,539,888 | 11/1970 | Prisco et al. | 318/116 |
| 3,673,475 | 6/1972 | Britton, Jr. | 318/122 |
| 3,787,715 | 1/1974 | Eaton, Jr. | 318/130 |
| 4,056,761 | 11/1977 | Jacoby | 318/118 X |
| 4,069,444 | 1/1978 | Heim | 318/118 X |
| 4,101,816 | 7/1978 | Shepter | 318/130 |

Primary Examiner—B. Dobeck

[57] ABSTRACT

Circuitry is disclosed for driving the transducer assembly of a dental handpiece at its resonant frequency. The circuitry includes a variable frequency oscillator and a peak-detecting processor which allows the oscillator to sweep through a continuum of frequencies until maximum current in the transducer driving coil is sensed.

9 Claims, 2 Drawing Figures

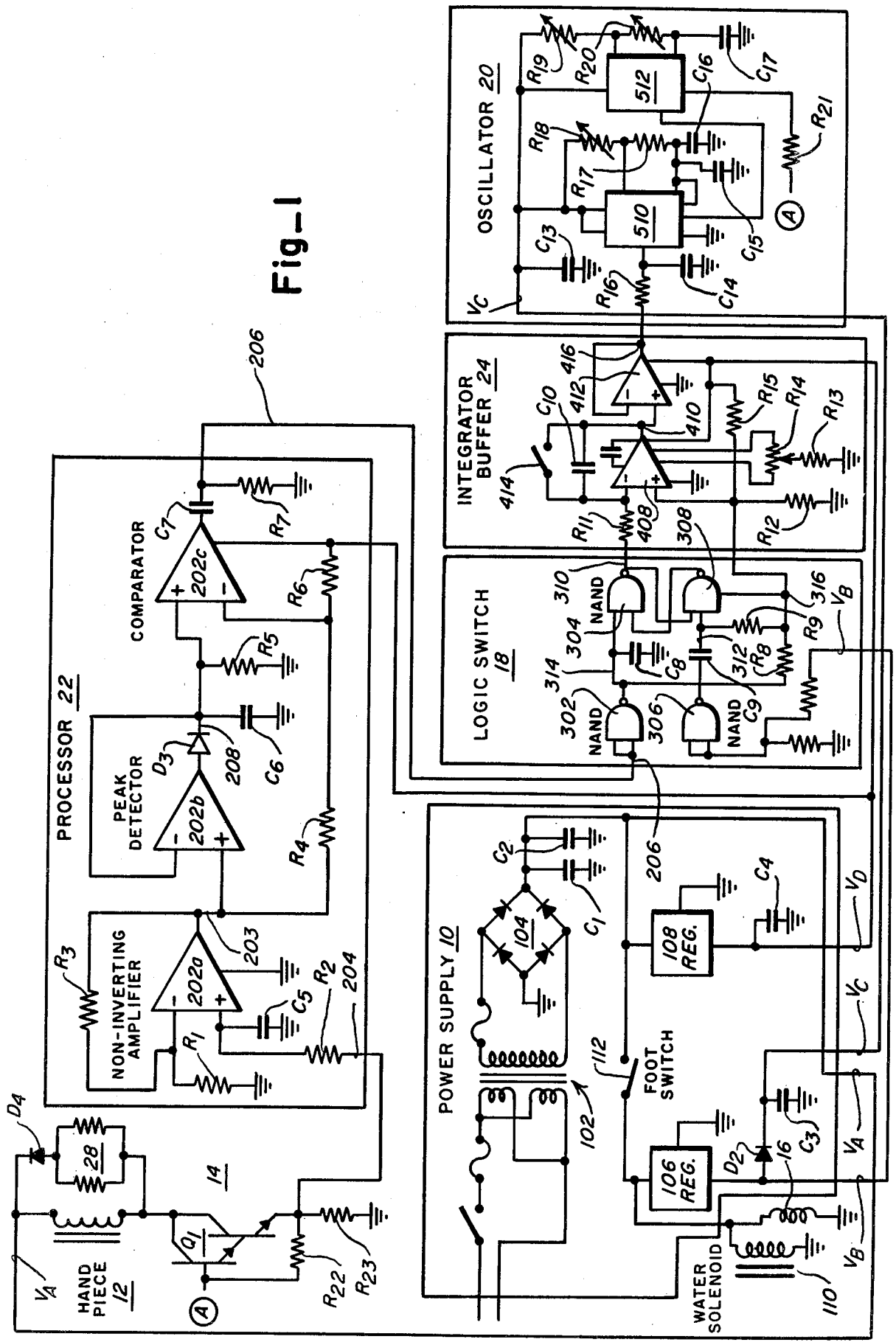
Fig_1

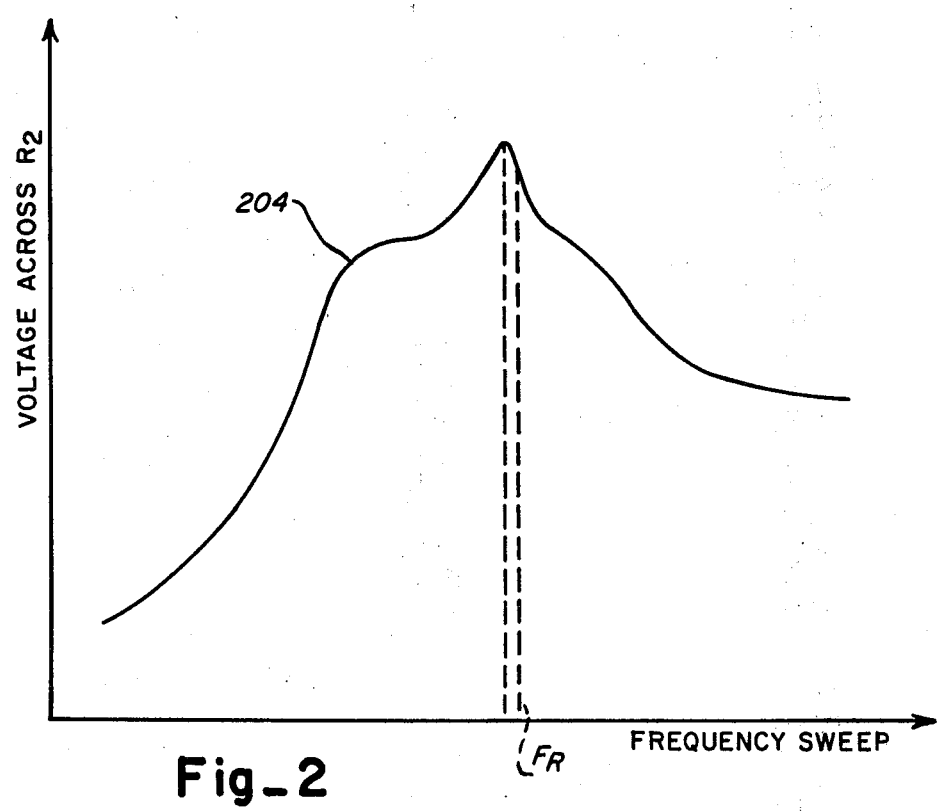
Fig_2

CIRCUIT FOR DRIVING AN ULTRASONIC DENTAL TOOL AT ITS RESONANT FREQUENCY

This is a continuation of application Ser. No. 903,888 filed May 8, 1978 now abandoned.

BACKGROUND OF THE INVENTION

This invention relates generally to electromechanical resonant systems, and more particularly is directed to improvements in electromechanical systems of the type in which high frequency vibrations are generated in a transducer by means of a driving coil through which an alternating current is fed from a variable frequency oscillator.

Electromechanical resonant systems of the type described herein are suitable for use with ultrasonic dental handpieces wherein the work tool is coupled to the transducer for longitudinal vibration thereby via a connecting body which may also act as an acoustical impedance transformer. As is known in the art, maximum vibration amplitude is obtained when the vibration frequency is at the resonant frequency of the transducer, tool holder and work tool. The resonant frequency is typically such that the overall length of the vibrating structure is an integral number of half-wavelengths of the longitudinal vibrations, although, as set forth in my co-pending U.S. Patent Application, Ser. No. 692,291 filed June 3, 1976, the relationship between the length of the foregoing assembly and the frequency of vibration need not be in terms of half-wavelengths.

In order to obtain the optimum amplitude of vibration, the frequency of the electrical oscillations within the transducer driving coil must be correlated to the natural frequency of vibration of the mechanical portion of the system.

DESCRIPTION OF THE PRIOR ART

U.S. Pat. No. 2,872,578 provides for the adjustment of the frequency of the oscillator generator either manually by an operator, or automatically under the control of a feedback signal which varies of the impedance of the transducer, or in accordance with a feedback signal obtained from a pickup such as a piezoelectric crystal which is coupled to the mechanically vibrating part of the resonant system.

U.S. Pat. No. 3,151,284 discloses another embodiment wherein the pickup means generating the feedback signal comprises a coil in surrounding relationship to the transducer. The pickup coil provides a feedback voltage which is used to control the oscillator.

U.S. Pat. No. 3,727,112 shows another embodiment utilizing a pickup coil.

U.S. Pat. No. 3,629,726 discloses an oscillator and an oscillator control circuit wherein a feedback voltage corresponding to the difference between the current through the transducer and the voltage across the transducer is utilized. The oscillator circuit receives feedback signals which are representative of both the voltage across and the current through the transducer driving coil and the two feedback signals are combined vectorally to block the oscillator frequency to the resonant frequency of the transducer.

SUMMARY OF THE INVENTION

An electrical circuit for driving the transducer assembly at essentially the resonant frequency of the assembly is provided comprising a variable frequency oscillator means responsive to a control signal to produce the alternating signal at a selected frequency within a range of frequencies, current sensing means for producing a feedback signal indicative of the magnitude of current flowing through the transducer driving coil, means for applying a variable control signal to the oscillator means to sweep the oscillator means through a spectrum of frequencies, and slope-detecting means responsive to the zero-crossing of the derivative of the feedback signal for sustaining the corresponding control signal, whereby the oscillator means is operative at the resonant frequency of the transducer.

BRIEF DESCRIPTION OF THE DRAWING

FIG. 1 is a schematic representation of an electrical circuit for driving the transducer assembly of a dental handpiece at essentially its resonant frequency, and FIG. 2 is a graphic representation showing the relationship between current flow through the transducer driving coil and oscillator frequency.

DESCRIPTION OF THE PREFERRED EMBODIMENT

FIG. 1 is a schematic representation of an electrical circuit constructed in accordance with the invention for driving the transducer assembly of a dental handpiece at essentially the resonant frequency of the transducer assembly. The circuit is generally shown to comprise a variable frequency oscillator 20 which operates through an output amplifier 14 to produce an alternating signal in the driving coil 12 of the handpiece. The frequency of the oscillator 20 is controlled by a control signal produced by an integrator buffer 24, as described in more detail below.

The system cycle is initiated with the activation by the dentist of a footswitch 112 associated with the powersupply 10. A voltage $V_b$ sets a logic switch 18 to produce a "start" signal 310. The integrator buffer 24 is responsive to the start signal 310 to produce a generally ramp-shaped control signal 416 which sweeps the oscillator 20 through a plurality of frequencies. A processor 22 monitors the coil 12 current to produce a "stop" signal when the oscillator is sweeping through the resonant frequency. The "stop" signal resets the logic switch 18 to hold the buffer 24 at the appropriate control signal value.

A brief reference to FIG. 2, which is a graphic illustration of the coil 12 current as a function of oscillator frequency shows that the voltage across the sensing resistor will increase to a maximum value at the resonant frequency and then decrease as the frequency is varied past the resonant frequency. The processor 22 is responsive to the reversal in the direction of coil current change as the oscillator sweeps through the resonant frequency.

Turning to a more detailed description of the circuitry, and with initial attention to the oscillator 20, a monolithic timing circuit is illustrated comprising two separate timers, 510, 512 which operate in the astable mode. Timer 510 functions as the basic oscillator and has a frequency which is determined by R17, R18, C15, and C16. The timer 510 includes a VCO input terminal which is connected to C14 and R16. The value of R16 determines the operating frequency range of the VCO system. C14 and C13 bypass high frequency noise. The output of timer 510 is fed to timer 512 which, as indicated above, forms another astable oscillator, with R19, R20 and C17 determining the duty cycle of the output signal delivered through R21 to the output amplifier 14. In the disclosed embodiment, the oscillator 20 provides a stable VCO oscillator frequency having a variable duty cycle. Naturally, the timer 512 can also be a monostable multivibrator triggered by an astable oscillator section 510.

The output amplifier 14 preferably comprises a Darlington pair of transistors Q1. The variable duty cycle wave form is applied to the base of the Darlington pair Q1, causing it to saturate and draw current through the coil 12. A damping resistor R28 and diode D4 are coupled in parallel with the handpiece coil in the collector circuit of the Darlington pair Q1. A resistor 23, located in the emitter circuit of the Darlington pair Q1 produces a voltage 204 which is responsive to the current flow through the handpiece coil 12. The voltage 204 is sensed by the processor 22.

The processor 22 basically comprises a non-inverting amplifier 202a, a peak detector 202b and a comparitor 202c. The voltage 204, which is initially a composite AC and DC voltage is filtered by the capacitor C5, the remaining average DC voltage being applied to the non-inverting input of the amplifier 202a. The gain of the amplifier 202a is determined, as known in the art, by the values of resistors R1 and R3. The amplified DC voltage 203 is applied to the input of the peak detector 202b and, simultaneously, to the inverting input terminal of the comparitor 202c via a resistor R4.

The peak detector 202b operates as an ideal diode with a capacitor C6 storing a DC voltage equal to the peak value of the voltage 203. This maximum value is applied to the non-inverting input of the comparitor 202c, while the instantaneous value of the voltage 203 is, as indicated above, applied to the inverting input of the comparitor 202c in combination with a small positive voltage from resistor R6 which provides a turn-on threshold. It will be appreciated that as the oscillator 20 sweeps towards the resonant frequency of the transducer assembly, both the inverting and non-inverting comparitor inputs will follow the rising value of the signal 203 as the coil current increases. The magnitude of coil current reaches a peak at the transducer resonant frequency, so that a further change in oscillator frequency reduces the current level and, accordingly, the value of the voltage 203. The capacitor C6 is left in a charged state at a level corresponding to the maximum level of signal 203 and is bled off at a time constant determined by the capacitor C6 and the resistor R5.

The comparitor 202c, which has been held in an OFF condition until the voltage from the peak detector 202b exceeds the voltage applied to the inverting terminal, turns on and propogates a pulse through the capacitor C7 to the input of the logic switch 18.

The logic switch 18 is shown comprising four 2-input COS/MOS/NAND gates 302, 304, 306, 308. Gates 304, 308 are connected to form a flip-flop, while gates 302, 306 are used as inverters. As shown, the truth table for NAND gates is:

| INPUT | OUTPUT |
|---|---|
| 00 | 1 |
| 01 | 1 |
| 10 | 1 |
| 11 | 0 |

The correct initialization of the flip-flop is guaranteed by a two-step process when power is applied to the system. Owing to the initially uncharged state of capacitor 305, the initial treatment state of the gates is:

| 302 | 304 |
|---|---|
| In  Out | Out |
| 0    0 | 1 |
| 306 | 308 |
| In  Out | Out |
| 0    1 | 1 | and the second, and stable, condition is:

| 302 | 304 |
|---|---|
| In  Out | Out |
| 0    1 | 1 |
| 306 | 308 |
| In  Out | Out |
| 0    1 | 0 |

Closing of the footswitch 112 applies $V_b$ to the input of gate 306 resulting in logic states of

| 302 | 304 |
|---|---|
| In  Out | Out |
| 0    1 | 0 |
| 306 | 308 |
| In  Out | Out |
| 1    0 | 1 |

As described below, the integrator buffer 24 will consequently integrate until a latching signal from the processor 22 signifies that the resonant frequency of the transducer is attached. The latching signal causes the flip-flop to shift in a two-step process as shown, causing the integrator to hold its output level.

| TRANSIENT | | STABLE | |
|---|---|---|---|
| 302 | 304 | 302 | 304 |
| In  Out | Out | In  Out | Out |
| 1    0 | 1 | 0    1 | 1 |
| 306 | 308 | 306 | 308 |
| In  Out | Out | In  Out | Out |
| 1    0 | 0 | 1    0 | 0 |

The integrator buffer 24 includes an integrator amplifier 408 which integrates the signal 310 from the logic switch 18. The charging current of the integrator capacitor C10 is proportional to the current flowing in the input resistor R11. The output voltage 410 from the integrator 408 is proportional to the voltage across the capacitor C10. Resistors R12 and R15 form a voltage divider which produces a reference starting voltage at the output of the integrator 408. Buffer amplifier 412 is coupled to the output of the integrator 408 as a voltage follower to isolate the oscillator 20 input signal from the discharge current of capacitor C10. Resistors R13 and R14 form a voltage null network which cancels input offset voltages caused by the logic switch 18. During the system cycle the capacitor C10 will therefore not charge or discharge after the integration period. Release of the footswitch 112 at the end of the cycle, deactivates the relay 16, to discharge the capacitor C10 through normally closed contact 414.

In operation, the application of AC line voltage to the system of FIG. 1 produces a DC voltage VA at the driving coil 12. The Darlington pair Q1 of the output amplifier 14 does not conduct, however, because the oscillator signal is not applied to the base of the Darlington pair Q1 until a footswitch 112, associated with the power supply 10, is closed.

Prior to the closing of the footswitch, DC voltage VD is applied to the processor 22 and the integrator buffer 24, and through voltage divider network of R15 and R12, to the logic switch 18.

The output of the logic switch 18 is at the same potential as its supply voltage, which is derived from the voltage divider network of resistors R15 and R12. The potential across the input of the integrator amplifier 408 is therefore zero and no charging current is applied to the capacitor C10. The switch 414, shunting the integrated capacitor C10, is a normally closed contact of a relay 16 coupled between the footswitch 112 and common. Accordingly, capacitor C10 is shunted by switch 414 until the closing of the footswitch 112.

The closing of the footswitch 112 applies a voltage to the water solenoid 110 and the voltage regulator 106 of the power supply 10. The output from the voltage regulator 106 is applied across a diode D2 to the oscillator 20, which in turn applies alternating input current to the base of the Darlington pair Q1. At the same time, the relay 16 is energized, opening the switch 414 in the integrator buffer 24 and removing the shunt from the capacitor C10. The logic switch 18 switches the state of the flip-flop combination 304, 308 causing signal 310 to go LO and thereby inducing a current through the resistor R11 to cause the capacitor C10 to charge upward at a substantially linear rate.

The charging potential of the capacitor C10 is coupled through the buffer amplifier 412 as the control signal to the oscillator 20. The linearly increasing control signal causes the oscillator 20 to shift frequency at the charge rate of the capacitor C10. Back at the processor 22, the peak detector 202b senses the amplified signal from the sensing resistor R23. As the oscillator is swept past the resonant frequency of the transducer assembly, the sensed signal level starts to decrease. The previous maximum signal stored in the capacitor C6 is compared to the now-decreasing sensed signal 203 by the comparitor 202c, causing the comparitor to change state. The output state of the comparitor is transformed to a pulse by the combination of capacitor C7 and resistor R7, and the pulse changes the logic state of NAND gate 302, thereby changing the output of signal 310 of the NAND gate 304 to a HI state. The HI state stops the current flow into the input of the integrating amplifier 408, thereby maintaining the output voltage of the integrating amplifier 408 (and the control voltage 416 to the oscillator), at a level which maintains the oscillator frequency at the resonant frequency. The cycle is repeated every time the footswitch is energized, keeping the oscillator frequency at essentially the resonant frequency of the transducer assembly.

While the foregoing description concerns a preferred embodiment of the present invention, it is understood that many variations and modifications are obvious to those skilled in the art. Accordingly, the present invention is to be defined only in terms of the appended claims which should be construed to include those variations and modifications.

I claim:

1. For use with a dental handpiece of the type adapted to hold a work tool and including
   a transducer assembly for receiving the tool as part of the assembly and which in turn includes means for producing a vibratory motion in the tool in response to an electrical signal of alternating polarity, and
   an electrical circuit for driving the transducer assembly at essentially the resonant frequency of the assembly and comprising:
   variable-frequency oscillator means responsive to a control signal to produce the alternating signal at a selected frequency within a range of frequencies;
   current-sensing means for producing a feedback signal indicative of the magnitude of current flow through the motion-producing means;
   slope-detecting means responsive to the zero-crossing of the feedback signal derivative for producing a latching signal; and
   means for applying a variable control signal to the oscillator means to sweep the oscillator means through a spectrum of frequencies, and including means responsive to the latching signal to stop the sweep at the frequency producing maximum current flow through the motion-producing means.

2. The circuit of claim 1 wherein the slope-detecting means includes
   memory means for storing successive maximum values of the feedback signal
   comparitor means for monitoring the feedback signal for comparison with the stored maximum value to produce a latching signal when the monitored signal is less than the maximum.

3. The circuit of claim 2 wherein the memory means includes
   first amplifier having a non-inverting input coupled to the sensing means, its output coupled to the anode of a unidirectional current flow device, and an inverting input to the cathode of said unidirectional current flow device, and
   capacitor means coupled between said cathode and a point of reference potential.

4. The circuit of claim 2 wherein the comparator means includes
   bistable amplifier means having an inverting input coupled to the sensing means, a non-inverting input coupled to the memory means, and an output coupled to the control signal producing means.

5. The circuit of claim 1 wherein the control signal means includes
   integrator amplifier means for producing a control signal having a time-proportional variation.

6. The circuit of claim 3 wherein the comparator means includes a bistable amplifier having an inverting input coupled to the feedback signal, a non-inverting input coupled electrically interjacent the capacitor means and the cathode of the unidirectional current flow device.

7. The circuit of claim 6 wherein the unidirectional current flow device is a diode.

8. The circuit of claim 5 wherein the latching signal-responsive means includes multivibrator means responsive to the latching signal to undergo a change from first to second states and for producing a state-indicative signal,
   the integrator amplifier means being operatively coupled thereto so as to produce an oscillator-sweeping control signal during the first state and to produce a frequency-maintaining control signal during the second state.

9. The circuit of claim 8 wheren the state-indicative signal is coupled to the integrator amplifier as the signal to be integrated.

* * * * *